United States Patent [19]

Loblaw et al.

[11] Patent Number: 4,560,638
[45] Date of Patent: Dec. 24, 1985

[54] HALFTONE IMAGING SILVER HALIDE EMULSIONS, PHOTOGRAPHIC ELEMENTS, AND PROCESSES WHICH EMPLOY NOVEL ARYLHYDRAZIDES

[75] Inventors: James C. Loblaw, Webster; Barbara B. Lussier, Rochester, both of N.Y.

[73] Assignee: Eastman Kodak Company, Rochester, N.Y.

[21] Appl. No.: 658,921

[22] Filed: Oct. 9, 1984

[51] Int. Cl.$^4$ .......................... G03C 1/06; G03C 1/02
[52] U.S. Cl. .................................. 430/264; 430/564; 430/567; 430/599; 430/603; 430/607; 430/611; 430/949; 430/600; 430/613
[58] Field of Search .............. 430/949, 264, 564, 567, 430/599, 603, 607, 611

[56] References Cited

U.S. PATENT DOCUMENTS

| | | | |
|---|---|---|---|
| 2,419,975 | 5/1947 | Trivelli et al. | 95/6 |
| 2,563,785 | 8/1981 | Ives | 95/88 |
| 3,227,552 | 1/1966 | Whitmore | 96/3 |
| 4,030,925 | 6/1977 | Leone et al. | 96/73 |
| 4,031,127 | 6/1977 | Leone et al. | 260/465 D |
| 4,080,207 | 3/1978 | Leone et al. | 96/73 |
| 4,168,977 | 9/1979 | Takada et al. | 96/63 |
| 4,221,857 | 9/1980 | Okutsu et al. | 430/264 |
| 4,224,401 | 9/1980 | Takada et al. | 430/437 |
| 4,225,511 | 3/1981 | Hirano et al. | 430/217 |
| 4,243,739 | 1/1981 | Mifune et al. | 430/266 |
| 4,245,037 | 1/1978 | Tsujino et al. | 430/559 |
| 4,266,013 | 5/1981 | Adachi et al. | 430/410 |
| 4,269,929 | 5/1981 | Nothnagle | 430/264 |
| 4,272,614 | 6/1981 | Mifune et al. | 430/441 |
| 4,276,364 | 6/1981 | Leone | 430/212 |
| 4,323,643 | 4/1982 | Mifune et al. | 430/441 |
| 4,459,347 | 7/1984 | Parton et al. | 430/217 |
| 4,478,928 | 10/1984 | Hess et al. | |

FOREIGN PATENT DOCUMENTS 126698 10/1975 Japan .

OTHER PUBLICATIONS

*Research Disclosure*, vol. 151, Nov., 1976, Item 15162.
Sidhu et al., *Research Disclosure*, vol. 176, Dec., 1978, Item 17626.
*Research Disclosure*, vol. 235, Nov., 1983, Item 23510.

*Primary Examiner*—Mary F. Downey
*Attorney, Agent, or Firm*—Carl O. Thomas

[57] ABSTRACT

An unballasted arylhydrazide is disclosed the aryl moiety of which is substituted with a group of the formula

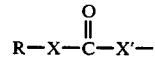

where one of X and X' represents —NH—, the other represents a divalent chalcogen, and R represents an aliphatic or aromatic residue. The arylhydrazides, when applied to halftone imaging in conjunction with silver halide emulsions, photographic elements, and imaging processes, produce images of improved dot quality and low levels of pepper fog.

14 Claims, 2 Drawing Figures

HALFTONE IMAGING SILVER HALIDE EMULSIONS, PHOTOGRAPHIC ELEMENTS, AND PROCESSES WHICH EMPLOY NOVEL ARYLHYDRAZIDES

FIELD OF THE INVENTION

The invention is directed to novel unballasted arylhydrazides, to silver halide emulsions and photographic elements capable of producing halftone images, and to processes for their use.

BACKGROUND OF THE INVENTION

Lithographic printing plates contain areas that accept ink, areas that repel ink, and, ideally, no areas of intermediate properties. The illusion that some areas of a printed image are of intermediate density is created by the viewer's inability to resolve tiny dots of maximum density and background areas of minimum density that separate them. Such images are referred to as halftone images.

Halftone images are typically produced on lithographic printing plates by contact exposure through a high contrast photographic transparency—often referred to as a lith type photographic element. To be useful for the exposure of lithographic printing plates the photographic element must have a contrast of at least 10 (hereinafter designated by reference to high contrast) and more typically near or above 20. Over and above contrast requirements, however, it is important that a lith type photographic element applied to halftone imaging exhibit the characteristic of producing high dot quality. That is, the dots must be well resolved—e.g., with sharp as opposed to soft or ragged edges.

The use of hydrazines in negative working surface latent image forming silver halide emulsions and photographic elements to increase speed and contrast is taught by Trivelli et al U.S. Pat. No. 2,419,975. Increased contrast attributable to hydrazines in negative working surface latent image forming silver halide emulsions is believed to result from the promotion of infectious development.

The hydrazines preferred for their higher effectiveness in increasing contrast are arylhydrazides. The acyl moiety of arylhydrazides increases activity while the aryl moiety acts to increase stability. The following are illustrative of specific arylhydrazides employed with negative working surface latent image forming silver halide emulsions primarily to increase contrast:

P-1 Takada et al U.S. Pat. No. 4,168,977
P-2 Takada et al U.S. Pat. No. 4,224,401
P-3 Okutsu et al U.S. Pat. No. 4,221,857
P-4 Mifune et al U.S. Pat. No. 4,243,739
P-5 Mifune et al U.S. Pat. No. 4,272,614
P-6 Mifune et al U.S. Pat. No. 4,323,643.

While the arylhydrazide is preferably incorporated directly in a photographic element, it can be incorporated in a processing solution for the element. A preferred processing solution is disclosed in the following patent:

P-7 Nothnagle U.S. Pat. No. 4,269,929.

In surface latent image forming silver halide emulsons the grains which are exposed to light are rendered developable while grains which are not exposed to light are not intended to be developed. Nevertheless, some of these unexposed grains develop spontaneously. In fulltone imaging the spontaneously developing grains raise minimum density more or less uniformly. Such minimum density levels are referred to as fog and, so long as they remain low, are not objectionable.

Figure 1:
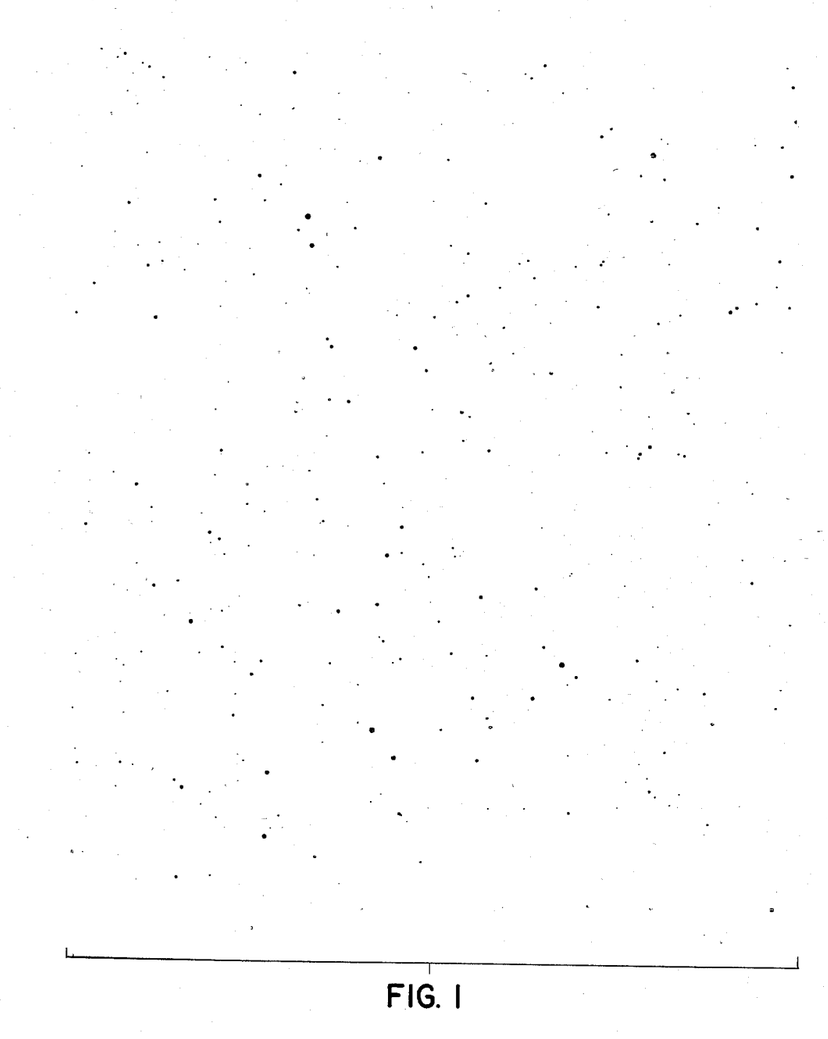
FIG. 1 is a photograph enlarged 20× showing a typical pattern of severe pepper fog and FIG. 2 is a photographic enlarged 20× showing the highest acceptable level of pepper fog.
Figure 2:
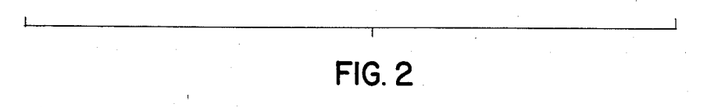

Pepper fog differs from ordinary fog in that it takes the form of small, maximum density areas randomly distributed on a substantially uniform minimum density background. When a photographic element exhibiting pepper fog is viewed under magnification, the impression to the viewer is often that the magnified field of view has been sprinkled with grains of pepper. It has been long recognized that arylhydrazides produce pepper fog, and, until very recently, this has interfered with the commercial use of arylhydrazides in halftone imaging. An illustration of severe pepper fog appears in FIG. 1. FIG. 2 is an illustration of pepper fog at its highest acceptable level. Each of FIGS. 1 and 2 is an actual photograph of a field of view enlarged 20×.

In addition to their use to increase contrast in negative working silver halide emulsions arylhydrazides have been employed extensively as nucleating agents in direct positive silver halide emulsions. When employed as a nucleating agent the function of the arylhydrazide is to replace uniform light exposure or aerial oxidation as a technique for selectively accelerating development of unexposed internal latent image forming silver halide grains. This increases maximum density without increasing minimum density of the direct positive image. The use of a hydrazine as a nucleating agent was first taught by P-8 Ives U.S. Pat. No. 2,563,785.

Exemplary arylhydrazides employed as nucleating agents in internal latent image forming direct positive emulsions are illustrated by the following:

P-9 Whitmore U.S. Pat. No. 3,227,552
P-10 Leone et al U.S. Pat. No. 4,030,925
P-11 Leone et al U.S. Pat. No. 4,031,127
P-12 Leone et al U.S. Pat. No. 4,080,207
P-13 Tsujino et al U.S. Pat. No. 4,245,037
P-14 Hirano et al U.S. Pat. No. 4,255,511
P-15 Adachi et al U.S. Pat. No. 4,266,013
P-16 Leone U.S. Pat. No. 4,276,364
   RD-1 *Research Disclosure*, Vol. 151, November 1976, Item 15162
   RD-2 Sidhu et al *Research Disclosure*, Vol. 176, December 1978, Item 17626

*Research Disclosure* is published by Kenneth Mason Publications, Ltd., The Old Harbourmaster's, 8 North Street, Emsworth, Hampshire P010 7DD, England.

Parton et al U.S. Pat. No. 4,459,347 discloses oxythioamido substituted arylhydrazides to be useful in increasing the speed of negative working surface latent image silver halide emulsions and as nucleating agents in direct positive internal latent image forming silver halide emulsions.

Hess et al U.S. Ser. No. 493,480, filed May 11, 1983, commonly assigned, discloses sulfinic acid radical substituted arylhydrazides to be effective for (i) increasing contrast of negative working surface latent image forming silver halide emulsions, (ii) nucleating direct positive internal latent image forming silver halide emulsions, and (iii) increasing the speed of negative working emulsions of less than high contrast when adsorbed to grain surfaces. For applications (i) and (ii) ballasting groups are disclosed, such as alkyl, alkoxy, amido, carbamoyl, oxyamido, carbamoyloxy, carboxy, oxycarbamoyl, phenyl, alkylphenyl, phenoxy, and alkylphenoxy groups as well as groups which are combinations thereof. For applications (ii) and (iii) the use an adsorption promoting moiety, such as an oxythioamido substituent, is disclosed.

A patent literature summary of arylhydrazides employed to increase contrast in negative working silver halide emulsions and to perform nucleation in direct positive silver halide emulsions, which includes a discussion of the mechanism of activity in each system is provided by the following publication:

RD-3 *Research Disclosure*, Vol. 235, November 1983, Item 23510.

An oxycarbamido substituent of an arylhydrazide is disclosed.

SUMMARY OF THE INVENTION

In one aspect this invention is directed to an unballasted arylhydrazide, the aryl moiety of which is substituted with a group of the formula (I)

where one of X and X' represents —NH—, the other represents a divalent chalcogen, and R represents an aliphatic or aromatic residue.

In another aspect this invention is directed to a high contrast negative working surface latent image forming silver halide emulsion comprised of an unballasted arylhydrazide, the aryl moiety of which is substituted with a group according to formula (I).

In still another aspect this invention is directed to a negative working photographic element capable of producing halftone images comprised of a support, an arylhydrazide, and a monodispersed surface latent image forming silver halide emulsion capable of producing a high contrast image in the presence of the arylhydrazide, further characterized in that the arylhydrazide is an unballasted arylhydrazide, the aryl moiety of which is substituted with a group according to formula (I).

In an additional aspect this invention is directed to an improved process for producing a halftone image by imagewise exposing through a halftone mask a negative working photographic element comprised of a support, an arylhydrazide, and a surface latent image forming silver halide emulsion capable of producing a high contrast image in the presence of the arylhydrazide, further characterized in that the arylhydrazide is an an unballasted arylhydrazide, the aryl moiety of which is substituted with a group according to formula (I).

It has been discovered that halftone images of good dot quality and acceptably low levels of pepper fog can be achieved when an unballasted arylhydrazide is employed containing an aryl substituent satisfying formula (I). Prior to this invention this desirable combination of properties has been achieved only by employing an arylhydrazide, the aryl moiety of which is substituted with a ureido group, in combination with a ballasted arylhydrazide. The requirement of a second arylhydrazide and, particularly, a ballasted arylhydrazide adds to the coating bulk of the photographic element. While a ureido substituted arylhydazide when employed in combination with a ballasted arylhydrazide, can increase dot quality, the proportion of the ureido substituted arylhydrazide must be limited to avoid unacceptably high levels of pepper fog. Thus, prior to the present invention the art has been faced with the limitations of (i) employing a combination of arylhydrazides and (ii) employing ureido substituted arylhydrazides within a narrow concentration range marked by poor dot quality on the lower border of the concentration range and unacceptably high pepper fog levels on the upper border of the concentration range. The present invention overcomes the limitations heretofore encountered in the art by allowing halftone images of good dot quality and acceptably low pepper fog levels to be achieved with a novel unballasted arylhydrazide that can be employed alone or, if desired, in combination with other conventional arylhydrazides within a wide range of relative proportions.

BRIEF DESCRIPTION OF THE DRAWINGS

The invention can be better appreciated by reference to the following detailed description considered in conjunction with the drawings, in which.

DESCRIPTION OF PREFERRED EMBODIMENTS

The advantages realized with the present invention can be primarily attributed to novel unballasted arylhydrazides, the aryl moiety of which is substituted with a group satisfying formula (I), as described above. An unballasted arylhydrazide within the contemplation of the present invention can be represented by the following formula:

(II)

wherein
Ac represents an activating group;
Ar represents a divalent aromatic group;
R represents an aliphatic or aromatic residue;
$R^1$ and $R^2$ can be either hydrogen or a sulfinic acid radical substituent, with the proviso that only one can be a sulfinic acid radical substituent; and
one of X and X' represents —NH— and the other represents a divalent chalcogen.

Although activating groups are not essential to increasing contrast with hydrazines, the most effective contrast increasing compounds are recognized to include at least one activating group. A variety of activating groups are described in RD-3, cited above. Preferred activating groups are acyl groups. Specifically preferred acyl groups can be represented by the formula:

(III)

where $R^3$ is hydrogen or an aliphatic or aromatic moiety. The highest activity levels are achieved when $R^3$ is hydrogen. In another preferred form $R^3$ can take the form of an alkyl group, with lower alkyl groups of from 1 to 3 carbon atoms being preferred, since activity for corresponding arylhydrazides generally declines as the number of carbon atoms forming the alkyl group increases. When $R^3$ is an aromatic moiety, it is preferably a phenyl group.

The divalent aromatic moiety Ar performs a stabilizing function by providing a direct linkage of the β nitrogen atom of the hydrazide to a tertiary carbon atom. In a preferred form the divalent aromatic moiety is a carbocyclic aromatic moiety—i.e., an arylene moiety, such as phenylene or naphthalene. In addition to the group represented by formula (I), the arylene moiety can be further ring substituted at any remaining available position. Examples of other useful substituents include hydroxy, amino, carboxy, alky, alkoxy, halo, and haloalkyl. As herein defined cycloalkyl is subsumed within alkyl moieties. Unless otherwise stated, all aliphatic and aromatic moieties referred to are understood to contain fewer than 8 carbon atoms. When Ar is a phenylene group, it can take the form of an o-, p-, or m-phenylene group, but it is most preferably a p-phenylene group with any additional substituents, if present, being preferably ortho substituents.

R can take the form of an aliphatic or aromatic residue. R should be chosen to retain mobility of the arylhydrazide in a silver halide emulsion or hydrophilic colloid layer of a photographic element. In one form R can be an arylhydrazide. For example, it can take any of the forms of the arylhydrazide shown to the right of X' in formula (II). In a prefered form R contains 8 or fewer carbon atoms. In a specifically preferred form R is an alkyl group, optimally an alkyl group containing from 2 to 6 carbon atoms. In an aromatic form R is preferably phenyl. Five and six member heterocyclic ring containing aromatic residues are also contemplated, such as pyridyl, thiazolyl, oxazolyl, and imidazolyl groups.

$R^1$ and $R^2$ are preferably hydrogen. It has been recognized that when one of the nitrogen atoms of the hydrazino moiety is displaced by a sulfinic acid radical substituent, preferably an arylsulfonyl group, an increase in photographic speed can be realized. As between $R^1$ and $R^2$ it is preferred that $R^1$ be a sulfinic acid radical substituent. However, photographic speeds fully acceptable for halftone imaging applications can be readily achieved in the absence of a sulfinic acid radical substituent attached to either of the nitrogen atoms α or β to the Ac moiety in formula (II), and overall characteristic curve shape in the toe and shoulder regions is generally superior in the absence of the sulfinic acid radical substituent.

When one of X and X' represents a divalent chalcogen (e.g., an oxy or thio linking atom), the other represents —NH—. When X is —NH—, X' can be chosen to complete a carbamoyloxy (—NH—C(O)—O—) or carbamoylthio (—NH—C(O)—S—) group. In a specifically prefered form of the invention X' is represented by —NH— and X completes a thiocarbamido (—S—C-(O)—NH—) and, most preferably, an oxycarbamido (—O—C(O)—NH—) group.

From the foregoing it is apparent that specifically preferred arylhydrazides according to the present invention can be represented by the following formula:

(IV)

where

Ar is a phenylene, preferably a p-phenylene, group;

R is alkyl of from 1 to 8 carbon atoms, preferably 2 to 6 carbon atoms, or a phenyl substituent; and $R^3$ is hydrogen, lower alkyl of from 1 to 3 carbon atoms, or phenyl.

The following are illustrative of specific arylhydrazides within the contemplation of this invention:

AH-1 2-(2,6-dichloro-4-methoxycarbamidophenyl)-1-propionylhydrazine

AH-2 2-(4-ethylcarbamoyloxyphenyl)-1-formylhydrazine

AH-3 2-(4-ethoxycarbamoylthiophenyl)-1-formylhydrazine

AH-4 2-(4-ethoxycarbamidophenyl)-1-formylhydrazine

AH-5 2-(4-ethoxycarbamidophenyl)-1-formyl-2-p-tosylhydrazine

AH-6 1-acetyl-2-(4-propoxycarbamidophenyl)hydrazine

AH-7 2-(4-butoxycarbamidophenyl)-1-formylhydrazine

AH-8 2-(4-butylthiocarbamidophenyl)-1-formylhydrazine

AH-9 2-(4-butylcarbamoyloxyphenyl)-1-formylhydrazine

AH-10 1-benzoyl-2-(4-butylcarbamoylthio-2-trifluoromethyl)hydrazine

AH-11 1-benzoyl-2-(2-pentoxycarbamidophenyl)hydrazine

AH-12 2-(4-iso-propoxycarbamidophenyl)-1-formylhydrazine

AH-13 2-(4-hexoxycarbamidophenyl)-1-formylhydrazine

AH-14 1-formyl-2-(4-phenoxycarbamidophenyl)hydrazine

AH-15 1-formyl-2-(2-methoxy-4-N-pyridyloxycarbamidophenyl)hydrazine

AH-16 1-formyl-2-(2-N,N-diethylamino-4-phenylthiocarbamidophenyl)hydrazine

The arylhydrazides of this invention can be incorporated in the silver halide emulsion or other hydrophilic colloid layers of photographic elements in any effective concentration up to the limit of their solubility. Generally no advantage is realized from introducing concentrations above about $10^{-2}$ mole per mole of silver. Concentration of levels of at least $10^{-3}$ mole per mole of silver are generally employed. A preferred concentration range for high halftone dot quality is from above about $1.5 \times 10^{-3}$ to $2 \times 10^{-3}$ mole per mole of silver.

Athough not required, it is specifically recognized that the arylhydrazides of this invention can be employed in combination with conventional arylhydrazides, such as those disclosed in P-1 through P-6 and RD-3, cited above and here incorporated by reference, known to increase contrast in negative working surface latent image forming silver halide emulsions. When one or more additional arylhydrazides are employed, the total arylhydrazide concentration can still be maintained within the ranges indicated above, but the minimum concentration of the novel unballasted arylhydrazide can be reduced, with the preferred concentration of the novel unballasted arylhydrazide being at least $5 \times 10^{-4}$ mole per mole of silver. Generally the molar ratio of the novel unballasted arylhydrazide to other arylhydazide should be at least 1 to 2.

In one preferred form the arylhydrazides of this invention are employed in combination with conventional ballasted arylhydrazides. One or more ballasting moieties are preferably present in arylhydrazides incorporated in photographic elements for the purpose of restricting mobility of the arylhydrazides. Ballasted arylhydrazides, though restricted in their mobility, are not confined to silver halide grain surfaces and are to be distinguished from arylhydrazides having a silver halide grain adsorption promoting moiety, such as a thiocarbonyl moiety.

Suitable ballasting groups can take conventional forms. For example, the ballasting groups can be similar to those found in common incorporated couplers. Ballasting groups are generally recognized to require at least 8 carbon atoms and frequently contain 30 or more carbon atoms. The ballast groups typically contain aliphatic and/or aromatic groups that are relatively unreactive, such as alkyl, alkoxy, amido, carbamoyl, oxyamido, carbamoyloxy, carboxy, oxycarbonyl, phenyl, alkylphenyl, phenoxy, alkylphenoxy, and similar groups, with individual ballasts frequently being comprised of combinations of these groups. Ballasted arylhydrazides, though restricted in mobility, retain sufficient residual mobility to promote infectious development. Suitable ballasted arylhydrazides can be selected from among those disclosed by P-1 through P-6 and RD-3.

The arylhydrazide compounds are employed in combination with negative working photographic emulsions comprised of radiation sensitive silver halide grains capable of forming a surface latent image and a vehicle. The silver halide emulsions include the high chloride emulsions conventionally employed in forming lith photographic elements as well as silver bromide and silver bromoiodide emulsions, which are recognized in the art to be capable of attaining higher photographic speeds. Generally the iodide content of the silver halide emulsions is less than about 10 mole percent silver iodide, based on total silver halide.

The silver halide grains of the emulsions are capable of forming a surface latent image, as opposed to being of the internal latent image forming type. Surface latent image silver halide grains are employed in the overwhelming majority of negative working silver halide emulsions, whereas internal latent image forming silver halide grains, though capable of forming a negative image when developed in an internal developer, are usually employed with surface developers to form direct positive images. The distinction between surface latent image and internal latent image silver halide grains is generally well recognized in the art. Generally some additional ingredient or step is required in preparation to form silver halide grains capable of preferentially forming an internal latent image as compared to a surface latent image.

Although the difference between a negative image produced by a surface latent image emulsion and a positive image produced by an internal latent image emulsion when processed in a surface developer is a qualitative difference which is visually apparent to even the unskilled observer, a number of tests have been devised to distinguish quantitatively surface latent image forming and internal latent image forming emulsions. For example, according to one such test when the sensitivity resulting from surface development (A), described below, is greater than that resulting from internal development (B), described below, the emulsion being previously light exposed for a period of from 1 to 0.01 second, the emulsion is of a type which is "capable of forming a surface latent image" or, more succinctly, it is a surface latent image emulsion. The sensitivity is defined by the following equation:

$$S = \frac{100}{Eh}$$

in which S represents the sensitivity and Eh represents the quantity of exposure necessary to obtain a mean density—i.e., $\frac{1}{2}$ (D-max + D-min).

Surface Development (A)

The emulsion is processed at 20° C. for 10 minutes in a developer solution of the following composition:

| | |
|---|---|
| N—methyl-p-aminophenol hemisulfate | 2.5 g |
| Ascorbic acid | 10 g |
| Sodium metaborate (with 4 molecules of water) | 35 g |
| Potassium bromide | 1 g |
| Water to bring the total to | 1 liter. |

Internal Development (B)

The emulsion is processed at about 20° C. for 10 minutes in a bleaching solution containing 3 g of potassium ferricyanide per liter and 0.0125 g of phenosafranine per liter and washed with water for 10 minutes and developed at 20° C. for 10 minutes in a developer solution having the following composition:

| | |
|---|---|
| N—methyl-p-aminophenol hemisulfate | 2.5 g |
| Ascorbic acid | 10 g |
| Sodium metaborate (with 4 moles of water) | 35 g |
| Potassium bromide | 1 g |
| Sodium thiosulfate | 3 g |
| Water to bring the total to | 1 liter. |

The silver halide grains, when the emulsions are used for lith applications, have a mean grain size of not larger than about 0.7 micron, preferably about 0.4 micron or less. Mean grain size is well understood by those skilled in the art, as illustrated by Mees and James, *The Theory of the Photographic Process*, 3rd Ed., MacMillan 1966, Chapter 1, pages 36–43. The photographic emulsions of this invention are capable of producing higher photographic speeds than would be expected from their mean grain sizes. The photographic emulsions can be coated to provide emulsion layers in the photographic elements of any conventional silver coverage. Common conventional silver coating coverages fall within the range of from about 0.5 to about 10 grams per square meter.

As is generally recognized in the art, higher contrasts can be achieved by employing relatively monodispersed emulsions, particularly when larger grain size emulsions are employed. As herein employed, the term "monodispersed" is employed to indicate emulsions having a coefficient of variation of less than 20%. For the highest levels of contrast it is generally preferred that the monodispersed emulsions have a coefficient of variation of less than 10%. (As employed herein the coefficient of variation is defined as 100 times the standard deviation of the grain diameter divided by the average grain diameter.)

Silver halide emulsions contain in addition to silver halide grains a vehicle. The proportion of vehicle can be widely varied, but typically is within the range of from about 20 to 250 grams per mole of silver halide. Excessive vehicle can have the effect of reducing maximum density and consequently also reducing contrast.

Thus for contrast values of 10 or more it is preferred that the vehicle be present in a concentration of 250 grams per mole of silver halide or less. The specific vehicle materials present in the emulsion and any other layers of the photographic elements can be chosen from among conventional vehicle materials. Preferred vehicles are water permeable hydrophilic colloids employed alone or in combination with extenders such as synthetic polymeric peptizers, carriers, latices, and binders. Such materials are more specifically described in *Research Disclosure*, Vol. 176, December 1978, Item 17643, Section IX. Vehicles are commonly employed with one or more hardeners, such as those described in Section X.

Emulsions according to this invention having silver halide grains of any conventional geometric form (e.g., regular octahedral or, preferably, cubic crystalline form) can be prepared by a variety of techniques—e.g., single-jet, double-jet (including continuous removal techniques), accelerated flow rate and interrupted precipitation techniques, as illustrated by Trivelli and Smith, *The Photographic Journal*, Vol. LXXIX, May, 1939, pages 330–338; T. H. James *The Theory of the Photographic Process*, 4th Ed., Macmillan, 1977, Chapter 3; Terwilliger et al *Research Disclosure*, Vol. 149, September 1976, Item 14987; *Research Disclosure*, Vol. 225, January 1983, Item 22534; as well as Nietz et al U.S. Pat. No. 2,222,264; Wilgus German OLS No. 2,107,118; Lewis U.K. Pat. Nos. 1,335,925, 1,430,465 and 1,469,480; Irie et al U.S. Pat. No. 3,650,757; Morgan U.S. Pat. No. 3,917,485 (where pAg cycling is limited to permit surface development); and Musliner U.S. Pat. No. 3,790,387. Double-jet accelerated flow rate precipitation techniques are preferred for forming monodispersed emulsions. Sensitizing compounds, such as compounds of copper, thallium, cadmium, rhodium, tungsten, thorium, iridium and mixtures thereof, can be present during precipitation of the silver halide emulsion, as illustrated by Arnold et al U.S. Pat. No. 1,195,432; Hochstetter U.S. Pat. No. 1,951,933; Trivelli et al, U.S. Pat. No. 2,448,060; Overman U.S. Pat. No. 2,628,167; Mueller U.S. Pat. No. 2,950,972; Sidebotham U.S. Pat. No. 3,488,709; and Rosecrants et al U.S. Pat. No. 3,737,313.

The individual reactants can be added to the reaction vessel through surface or sub-surface delivery tubes by gravity feed or by delivery apparatus for maintaining control of the pH and/or pAg of the reaction vessel contents, as illustrated by Culhane et al U.S. Pat. No. 3,821,002, Oliver U.S. Pat. No. 3,031,304 and Claes et al *Photographische Korrespondenz*, Band 102, Number 10, 1967, page 162. In order to obtain rapid distribution of the reactants within the reaction vessel, specially constructed mixing devices can be employed, as illustrated by Audran U.S. Pat. No. 2,996,287, McCrossen et al U.S. Pat. No. 3,342,605, Frame et al U.S. Pat. No. 3,415,650, Porter et al U.S. Pat. No. 3,785,777, Saito et al German OLS No. 2,556,885 and Sato et al German OLS No. 2,555,365. An enclosed reaction vessel can be employed to receive and mix reactants upstream of the main reaction vessel, as illustrated by Forster et al U.S. Pat. No. 3,897,935 and Posse et al U.S. Pat. No. 3,790,386.

The grain size distribution of the silver halide emulsions can be controlled by silver halide grain separation techniques or by blending silver halide emulsions of differing grain sizes. The emulsions can include ammoniacal emulsions, as illustrated by Glafkides, *Photographic Chemistry*, Vol. 1, Fountain Press, London, 1958, pages 365–368 and pages 301–304; thiocyanate ripened emulsions, as illustrated by Illingsworth U.S. Pat. No. 3,320,069; thioether ripened emulsions as illustrated by McBride U.S. Pat. No. 3,271,157, Jones U.S. Pat. No. 3,574,628 and Rosecrants et al U.S. Pat. No. 3,737,313 or emulsions containing weak silver halide solvents, such as ammonium salts, as illustrated by Perignon U.S. Pat. No. 3,784,381 and *Research Disclosure*, Vol. 134, June 1975, Item 13452.

The silver halide emulsion can be unwashed or washed to remove soluble salts. The soluble salts can be removed by chill setting and leaching, as illustrated by Craft U.S. Pat. No. 2,316,845 and McFall et al U.S. Pat. No. 3,396,027; by coagulation washing, as illustrated by Hewitson et al U.S. Pat. No. 2,618,556, Yutzy et al U.S. Pat. No. 2,614,928, Yackel U.S. Pat. No. 2,565,418, Hart et al U.S. Pat. No. 3,241,969, Waller et al U.S. Pat. No. 2,489,341, Klinger U.K. Pat. No. 1,305,409 and Dersch et al U.K. Pat. No. 1,167,159; by centrifugation and decantation of a coagulated emulsion, as illustrated by Murray U.S. Pat. No. 2,463,794, Ujihara et al U.S. Pat. No. 3,707,378, Audran U.S. Pat. No. 2,996,287 and Timson U.S. Pat. No. 3,498,454; by employing hydrocyclones alone or in combination with centrifuges, as illustrated by U.K. Pat. No. 1,336,692, Claes U.K. Pat. No. 1,356,573 and Ushomirskii et al *Soviet Chemical Industry*, Vol. 6, No. 3, 1974, pages 181–185; by diafiltration with a semipermeable membrane, as illustrated by *Research Disclosure*, Vol. 102, October 1972, Item 10208, Hagemaier et al *Research Disclosure*, Vol. 131, March 1975, Item 13122, Bonnet *Research Disclosure*, Vol. 135, July 1975, Item 13577, Berg et al German OLS No. 2,436,461 and Bolton U.S. Pat. No. 2,495,918 or by employing an ion exchange resin, as illustrated by Maley U.S. Pat. No. 3,782,953 and Noble U.S. Pat. No. 2,827,428. The emulsions, with or without sensitizers, can be dried and stored prior to use as illustrated by *Research Disclosure*, Vol. 101, September 1972, Item 10152.

For high contrast photographic applications high levels of photographic speed are not necessarily required. Thus, the emulsions employed need not be chemically sensitized. Sensitization with one or more middle chalcogens, sulfur, selenium, and/or tellurium, is a preferred surface chemical sensitization. Such sensitization can be achieved by the use of active gelatin or by the addition of middle chalcogen sensitizers, such as disclosed by *Research Disclosure*, Item 17643, cited above, Section III. Reduction and other conventional chemical sensitization techniques disclosed therein which do not unacceptably reduce contrast can also be employed.

Spectral sensitization of the high contrast silver halide emulsions is not required, but can be undertaken using conventional spectral sensitizers, singly or in combination, as illustrated by *Research Disclosure*, Item 17643, cited above Section IV. For black-and-white imaging orthochromatic and panchromatic sensitizations are frequently preferred.

By suitable choice of substituent groups the dyes can be cationic, anionic or nonionic. Preferred dyes are cationic cyanine and merocyanine dyes. Emulsions containing cyanine and merocyanine dyes have been observed to exhibit relatively high contrasts. Spectral sensitizing dyes specifically preferred for use in the practice of this invention are as follows:

SS-1 Anhydro-5,5'-dichloro-9-ethyl-3,3'-bis-(3sulfopropyl)oxacarbocyanine hydroxide, sodium salt
SS-2 5,5',6,6'-Tetrachloro-1,1',3,3'-tetraethylbenzimidazolocarbocyanine iodide
SS-3 3,3'-Diethyl-9-methylthiacarbocyanine bromide
SS-4 3,3-Diethyloxacarbocyanine iodide
SS-5 5,5'-Dichloro-3,3',9-triethylthiacarbocyanine bromide
SS-6 3,3'-Diethylthiocarbocyanine iodide
SS-7 5,5'-Dichloro-2,2'-diethylthiocarbocyanine, p-toluene sulfonate salt
SS-8 3-Carboxymethyl-5-[(3-methyl-2-thiazolidinylidene)-2-methylethylidene]rhodanine
SS-9 3-Ethyl-3-[(3-ethyl-2-thiazolidinylidene)-2-methylethylidene]rhodanine
SS-10 5-[(3-{2-Carboxyethyl}-2-thiazolidinylidene)ethylidene]-3-ethylrhodanine
SS-11 1-Carboxymethyl-5-[(3-ethyl-2-benzothiazolinylidene)ethylidene]-3-phenyl-2-thiohydantoin
SS-12 1-Carboxymethyl-5-[(1-ethyl-2(H)-naphtho{1,2-d}thiazolin-2-ylidene)ethylidene]-3-phenyl-2-thiohydantoin
SS-13 3-Carboxymethyl-5-[(3-ethyl-2-benzothiazolinylidene)ethylidene]rhodanine
SS-14 5-[(3-Ethyl-2-benzoxazolinylidene)ethylidene]-3-heptyl-2-thio-2,4-oxazolidinedione
SS-15 3-Carboxymethyl-5-(3-ethyl-2-benzothiazolinylidene)rhodanine
SS-16 3-Carboxymethyl-5-(3-methyl-2-benzoxazolinylidene)rhodanine
SS-17 3-Ethyl-5-[(3-ethyl-2-benzoxazolinylidene)ethylidene]rhodanine The photographic elements can be protected against fog by incorporation of antifoggants and stabilizers in the element itself or in the developer in which the element is to be processed. Conventional antifoggants, such as those disclosed by Mifune et al U.S. Pat. Nos. 4,241,164, 4,311,781, 4,166,742, and 4,237,214, and Okutsu et al U.S. Pat. No. 4,221,857, can be employed.

Preferred antifoggants are benzotriazoles, such as benzotriazole (that is, the unsubstituted benzotriazole compound), halo-substituted benzotriazoles (e.g., 5-chlorobenzotriazole, 4-bromobenzotriazole, and 4-chlorobenzotriazole), and alkyl-substituted benzotriazoles wherein the alkyl moiety contains from about 1 to 12 carbon atoms (e.g., 5-methylbenzotriazole). Other known useful antifoggants include benzimidazoles, such as 5-nitrobenzimidazoles; benzothiazoles, such as 5-nitrobenzothiazole and 5-methylbenzothiazole; heterocyclic thiones, such as, 1-methyl-2-tetrazoline-5-thione; triazines, such as 2,4-dimethylamino-6-chloro-5-triazine; benzoxazoles, such as ethylbenzoxazole; and pyrroles, such as 2,5-dimethylpyrrole.

The antifoggants can be employed in conventional concentrations. The benzotriazole can be located in the emulsion layer or in any hydrophilic colloid layer of the photographic element in a concentration in the range of from $10^{-4}$ to $10^{-1}$, preferably $10^{-3}$ to $3 \times 10^{-2}$, mole per mole of silver. When the benzotriazole antifoggant is added to the developer, it is employed in a concentration of from $10^{-6}$ to about $10^{-1}$, preferably $3 \times 10^{-5}$ and $3 \times 10^{-2}$, mole per liter of developer.

In addition to the components of the photographic emulsions and other hydrophilic colloid layers described above it is appreciated that other conventional element addenda compatible with obtaining relatively high contrast silver images can be present. For example, the photographic elements can contain developing agents (described below in connection with the processing steps), development modifiers, plasticizers and lubricants, coating aids, antistatic materials, and matting agents, these conventional materials being illustrated in *Research Disclosure*, cited above, Item 17643, Sections XII, XIII, XVI, and XX. The elements can be exposed as described in Section XVIII.

The light sensitive silver halide contained in the photographic elements can be processed following exposure to form a relatively high contrast image by associating the silver halide with an aqueous alkaline medium in the presence of a developing agent contained in the medium or the element. Processing formulations and techniques are described in L. F. Mason, *Photographic Processing Chemistry*, Focal Press, London, 1966; *Processing Chemicals and Formulas*, Publication J-1, Eastman Kodak Company, 1973; *Photo-Lab Index*, Morgan and Morgan, Inc., Dobbs Ferry, New York 1977; and *Neblette's Handbook of Photographic and Reprographic Materials, Processes and Systems*, VanNostrand Reinhold Company, 7th Ed., 1977.

It is a distinct advantage of the present invention that the photographic elements can be processed in conventional developers generally as opposed to specialized developers conventionally employed in conjunction with lith photographic elements to obtain very high contrast images. When the photographic elements contain incorporated developing agents, the elements can be processed in an activator, which can be identical to the developer in composition, but lacking a developing agent. Very high contrast images can be obtained at pH values in the range of from 10 to 13.0, preferably 10.5 to 12.5. It is also an advantage of this invention that relatively high contrast images can be obtained with higher concentrations of preservatives to reduce aerial oxidation of the developing agents, such as alkali sulfites (e.g., sodium or potassium sulfite, bisulfite or metasulfite) than has heretofore been feasible in traditional lith processing. This allows the developers to be stored for longer periods. Any preservative or preservative concentration conventional in lower contrast processing can be employed, such as, for instance, a sulfite ion concentration in the range of from about 0.15 to 1.2 mole per liter of developer.

The developers are typically aqueous solutions, although organic solvents, such as diethylene glycol, can also be included to facilitate the solvency of organic components. The developers contain one or a combination of conventional developing agents, such as polyhydroxybenzene, aminophenol, para-phenylenediamine, ascorbic acid, pyrazolidone, pyrazolone, pyrimidine, dithionite, hydroxylamine or other conventional developing agents. It is preferred to employ hydroquinone and 3-pyrazolidone developing agents in combination. The pH of the developers can be adjusted with alkali metal hydroxides and carbonates, borax and other basic salts. To reduce gelatin swelling during development, compounds such as sodium sulfate can be incorporated into the developer. Also, compounds such as sodium thiocyanate can be present to reduce granularity. Also, chelating and sequestering agents, such as ethylenediaminetetraacetic acid or its sodium salt, can be present. Generally, any conventional developer composition can be employed in the practice of this invention. Specific illustrative photographic developers are disclosed in the *Handbook of Chemistry and Physics*, 36th Edition, under the title "Photographic Formulae" at page 3001 et seq., and in *Processing Chemicals and Formulas,* 6th Edition, published by Eastman Kodak Company (1963), the disclosures of which are here incorporated by reference. The photographic elements can, of course, be processed with conventional developers for lith photographic elements, as illustrated by Masseth U.S. Pat. No. 3,573,914 and VanReusel U.K. Pat. No. 1,376,600. A preferred developer is disclosed by P-7.

EXAMPLES

The invention can be better appreciated by reference to the following specific examples:

Comparative Coatings 1 through 12

Comparative Coatings 1 through 12 illustrate the poor level of pepper fog obtained when non-carbamate nucleating agents are used in a high-contrast lith film alone or in combination. The nucleating agents are 1-formyl-2-{4-[2-(2,4-di-t-pentylphenoxy)butyramido]-phenyl}hydrazine (N-1) and 1-[4-(2-formylhydrazino)-phenyl]-3-n-hexylurea (N-2).

On a polyester support was coated a layer comprising a monodispersed 0.22 $\mu$m AgBrI (2.5 mole % iodide) emulsion at 3.50 g/m$^2$ Ag, 2.47 g/m$^2$ gelatin, and 1.06 g/m$^2$ of a latex copolymer of methyl acrylate, 2-methyl-2-acrylamido-1-propane-sulfonic acid, and acetoacetoxyethyl methacrylate (90:4:6 monomer weight ratio). No chemical sensitization step was performed on the emulsion. The emulsion was spectrally sensitized with 216 mg/Ag mole of anhydro-5,5'-dichloro-9-ethyl-3,3'-di-(3-sulfopropyl)oxacarbocyanine hydroxide, triethylamine salt. Additions of nucleating agents N-1 and N-2 were made as listed in Table I, totaling $11 \times 10^{-4}$ moles/Ag mole. A protective overcoat of 1.38 g/m$^2$ gelatin was coated over the emulsion layer.

Samples of the coatings were exposed through a step tablet for 1 sec to a 600-watt 3000° K. quartz halogen source in an Eastman Model 1B Sensitometer and processed in a KODALITH Model 324 ® processor, with development in a developer of the type disclosed in U.S. Pat. No. 4,269,929 for 85 sec at 29.5° C. The speed, $\gamma$, and qualitatively rated dot quality and pepper fog levels are tabulated in Table I. The relative speeds are normalized to that of Coating 1 taken as 100.

The results of Table I show that combinations of nucleating agents N-1 and N-2 provided acceptable halftone image and pepper fog properties only in a single coating.

TABLE I

| Coating No. | Nucleators N-1 and N-2 | | Relative Speed | $\gamma$ | Dot Quality | Pepper Fog |
|---|---|---|---|---|---|---|
| | Moles $\times 10^4$ | | | | | |
| | N-1 | N-2 | | | | |
| C-1 | 11 | 0 | 100 | 9.5 | Soft Dots | None |
| C-2 | 10 | 1 | 162 | 15.8 | Soft Dots | None |
| C-3 | 9 | 2 | 276 | 23.3 | Marginal | None |
| C-4 | 8 | 3 | 302 | 24.2 | Good | Acceptable |
| C-5 | 7 | 4 | 309 | 24.3 | Good | Unacceptable |
| C-6 | 6 | 5 | 339 | 29.4 | Good | Unacceptable |
| C-7 | 5 | 6 | 389 | 30.1 | Good | Unacceptable |
| C-8 | 4 | 7 | 389 | 30.8 | Good | Unacceptable |
| C-9 | 3 | 8 | 363 | 35.8 | Good | Unacceptable |
| C-10 | 2 | 9 | 347 | 33.1 | Good | Unacceptable |
| C-11 | 1 | 10 | 363 | 31.3 | Good | Unacceptable |
| C-12 | 0 | 11 | 380 | 38.0 | Good | Severe |

Comparative Coatings 13 through 32

These coatings show that excellent half-tone dot quality with complete absence of pepper fog can be obtained by use of the combination of nucleating agent N-1 and a nucleating agent of the invention, 2-(4-n-butoxycarbamidophenyl)-1-formylhydrazine (AH-7).

The coatings were prepared, exposed, and processed as described above, but with nucleating agent additions as listed in Table II. A total nucleating agent level of $19 \times 10^{-4}$ moles per Ag mole was used in each coating. The results are tabulated in Table II. The relative speeds are normalized to that of Coating 1 of Table I taken as 100.

The results of Table II show that the combination of nucleating agents N-1 and AH-7 provided acceptable halftone image quality and pepper fog properties over a wide range of relative proportions. When nucleating agent AH-7 of the invention was used alone (Coating No. 32), excellent dot quality was obtained with only a slight level of pepper fog.

TABLE II

| Coating No. | Nucleating Agents N-1 and AH-7 | | Relative Speed | $\gamma$ | Dot Quality | Pepper Fog |
|---|---|---|---|---|---|---|
| | Moles $\times 10^4$ | | | | | |
| | N-1 | AH-7 | | | | |
| 13 | 19 | 0 | 89 | 10.4 | Soft Dots | None |
| 14 | 18 | 1 | 138 | 12.9 | Soft Dots | None |
| 15 | 17 | 2 | 214 | 13.8 | Soft Dots | None |
| 16 | 16 | 3 | 246 | 16.1 | Marginally Acceptable | None |
| 17 | 15 | 4 | 234 | 18.3 | Marginally Acceptable | None |
| 18 | 14 | 5 | 240 | 20.4 | Good | None |
| 19 | 13 | 6 | 276 | 19.2 | Good | None |
| 20 | 12 | 7 | 276 | 23.7 | Excellent | None |
| 21 | 11 | 8 | 276 | 24.9 | Excellent | None |
| 22 | 10 | 9 | 295 | 23.1 | Excellent | None |
| 23 | 9 | 10 | 276 | 20.7 | Excellent | None |
| 24 | 8 | 11 | 269 | 23.2 | Excellent | None |
| 25 | 7 | 12 | 295 | 25.2 | Excellent | None |
| 26 | 6 | 13 | 302 | 24.8 | Excellent | None |
| 27 | 5 | 14 | 289 | 24.3 | Excellent | None |
| 28 | 4 | 15 | 302 | 25.5 | Excellent | None |
| 29 | 3 | 16 | 295 | 24.3 | Excellent | None |
| 30 | 2 | 17 | 309 | 26.1 | Excellent | Very Slight |
| 31 | 1 | 18 | 309 | 25.6 | Excellent | Very Slight |
| 32 | 0 | 19 | 316 | 22.7 | Excellent | Slight |

Comparative Coatings 33 through 46

Comparative Example 3 shows that nucleating agent N-2 when used alone is unable to provide both good half-tone dot quality and an acceptable pepper fog level, while nucleating agent AH-7 of the invention used alone can provide excellent dot quality at an acceptable pepper fog level.

The coatings were prepared, exposed and processed as described above, but with the nucleating agent additions as listed in Table III. The results are tabulated in Table III, with the relative speeds normalized to that of Coating 1 of Table I taken as 100.

The results of Table III show that as the level of nucleating agent N-2 was increased, half-tone dot quality increased, but the pepper fog rapidly reached an unacceptable level. In the case of nucleating agent AH-7 of the invention, however, the pepper fog remained at a fully acceptable level while an excellent dot quality was achieved.

TABLE III

Nucleating Agents N-2 and AH-7

| Coating No. | Moles × 10⁴ N-2 | Moles × 10⁴ AH-7 | Relative Speed | γ | Dot Quality | Pepper Fog |
|---|---|---|---|---|---|---|
| 33 | 1 | 0 | 110 | 6.1 | Soft Dots | Acceptable |
| 34 | 2 | 0 | 214 | 12.7 | Soft Dots | Acceptable |
| 35 | 3 | 0 | 257 | 27.3 | Marginal | Acceptable |
| 36 | 4 | 0 | 295 | 15.6 | Good | Unacceptable |
| 37 | 5 | 0 | 309 | 19.5 | Good | Unacceptable |
| 48 | 6 | 0 | 331 | 27.6 | Good | Unacceptable |
| 39 | 0 | 12 | 240 | 16.4 | Marginal | Acceptable* |
| 40 | 0 | 13 | 246 | 16.5 | Marginal | Acceptable* |
| 41 | 0 | 14 | 257 | 18.1 | Good | Acceptable* |
| 42 | 0 | 15 | 257 | 17.4 | Good | Acceptable* |
| 43 | 0 | 16 | 269 | 19.3 | Excellent | Acceptable* |
| 44 | 0 | 17 | 282 | 17.4 | Excellent | Acceptable* |
| 45 | 0 | 18 | 282 | 20.3 | Excellent | Acceptable* |
| 46 | 0 | 19 | 289 | 18.2 | Excellent | Acceptable* |

*Pepper fog levels less than Coating 35

Investigations of 2-(4-hexoxycarbamidophenyl)-1-formylhydrazine (AH-13) and 1-formyl-2-(4-phenoxycarbamidophenyl)hydrazine (AH-14) also demonstrated satisfactory performance levels, whether employed alone or in combination with N-1.

Preparations of the novel unballasted arylhydrazides of this invention can be readily appreciated from the following illustrative preparation:

Preparation of 2-(4-ethylcarbamoyloxyphenyl)-1-formylhyrazine (AH-2)

Ethylchloroformate (9.01 g., 0.066 mol) was added dropwise to a suspension of 4-amino-1-(2'-formylhydrazino)benzene (10.0 g., 0.066 mol) and 2,6-lutidine (7.1 g, 0.066 mol) in acetonitrile (250 ml). Upon heating to reflux, the reaction mixture became homogeneous. After three hours the reaction had gone to completion as evidenced by thin layer chromatographic examination. The solvent was removed under reduced pressure. The resulting solid was slurried in water and filtered to remove any water soluble amine starting material. The collected solid was slurried in diethyl ether and filtered to remove ether soluble impurities. The collected solid was recrytallized from methanol to yield a white solid (11.4 g., 77% of theoretical yield, melting point 134° C.).

The invention has been described in detail with particular reference to preferred embodiments thereof, but it will be understood that variations and modifications can be effected within the spirit and scope of the invention.

What is claimed is:

1. A high contrast negative working surface latent image forming silver halide emulsion comprised of an unballasted arylhydrazide, the aryl moiety of which is substituted with a group of the formula:

where one of X and X' represents —NH—, the other represents a divalent chalcogen, and R represents an aliphatic or aromatic residue.

2. A high contrast negative working surface latent image forming silver halide emulsion according to claim 1 wherein R contains 8 or fewer carbon atoms.

3. A high contrast negative working surface latent image forming silver halide emulsion according to claim 1 wherein X' is —NH—.

4. A high contrast negative working surface latent image, forming silver halide emulsion according to claim 1 wherein X is —O— or —S—.

5. A high contrast negative working surface latent image forming silver halide emulsion according to claim 1 wherein said unballasted arylhydrazide is employed in a concentration of at least $10^{-3}$ mole per silver mole.

6. A high contrast negative working surface latent image forming silver halide emulsion according to claim 5 wherein R contains 2 to 6 carbon atoms, X is —O—, and X' is —NH—.

7. A high contrast negative working surface latent image forming silver halide emulsion according to claim 6 wherein said unballasted arylhydrazide is present in a concentration of from $1.5\times10^{-4}$ to $2\times10^{-4}$ mole per silver mole.

8. A high contrast negative working surface latent image silver halide emulsion according to claim 7 wherein R contains 2 to 6 carbon atoms, X is —O—, X' is —NH—, said unballasted arylhydrazide is present in combination with a ballasted arylhydrazide in a molar ratio of at least 1:2, and said unballasted arylhydrazide is present in a concentration of at least $5\times10^{-4}$.

9. A negative working photographic element capable of producing halftone images and comprised of a support, an arylhydrazide, and a monodispersed surface latent image forming silver halide emulsion capable of producing a high contrast image further characterized in that the arylhydrazide is an unballasted arylhydrazide, the aryl moiety of which is substituted with a group according to the formula:

where one of X and X' represents —NH—, the other represents a divalent chalcogen, and R represents an aliphatic or aromatic residue.

10. A negative working photographic element capable of producing halftone images comprised of a support and a high contrast surface latent image forming silver halide emulsion comprised of an unballasted arylhydrazide of the formula wherein
Ac represents Ar represents a divalent aromatic group;
R represents an aliphatic or aromatic residue;
$R^1$ and $R^2$ can be either hydrogen or a sulfinic acid radical substituent, with the proviso that only one can be a sulfinic acid radical substituent;
$R^3$ represents hydrogren, alkyl of from 1 to 3 carbon atoms, or phenyl; and one of X and X' represents —NH— and the other represents a divalent chalcogen.

11. A negative working photographic element capable of producing halftone images according to claim 10 wherein $R^3$ is hydrogen, Ar is a p-phenylene group, R is a phenyl or alkyl group of 8 or fewer carbon atoms, X is —O— or —S—, and X' is —NH—.

12. A process for producing a halftone image by imagewise exposing through a halftone mask a negative working photographic element comprised of a support, an arylhydrazide, and a surface latent image forming silver halide emulsion capable of producing a high contrast image in the presence of the arylhydrazide further characterized in that said arylhydrazide is an unballasted aryl hydrazide, the aryl moiety of which is substituted with a group according to the formula:

where one of X and X' represents —NH—, the other represents a divalent chalcogen, and R represents an aliphatic or aromatic residue.

13. A process for producing a halftone image by imagewise exposing through a halftone mask a negative working photographic element comprised of a support and a high contrast surface latent image forming silver halide emulsion comprised of an unballasted arylhydrazide of the formula wherein
Ac represents Ar represents a divalent aromatic group;
R represents an aliphatic or aromatic residue;
$R^1$ and $R^2$ can be either hydrogen or a sulfinic acid radical substituent, with the proviso that only one can be a sulfinic acid radical substituent;
$R^3$ represents hydrogen, alkyl of from 1 to 3 carbon atoms, or phenyl; and
one of X and X' represents —NH— and the other represents a divalent chalcogen.

14. A process for producing a halftone image by imagewise exposing through a halftone mask a negative working photographic element comprised of a support and a high contrast surface latent image forming silver halide emulsion comprised of an unballasted arylhydrazide of the formula wherein
Ac represents Ar represents a p-phenylene group;
R represents a phenyl group or an alkyl group of 2 to 6 carbon atoms;
$R^1$ and $R^2$ can be either hydrogen or a sulfinic acid radical substituent, with the proviso that only one can be a sulfinic acid radical substituent;
X is —O— or —S—; and
X' is —NH—.

* * * * *